(12) United States Patent
Sezginer

(10) Patent No.: US 7,046,376 B2
(45) Date of Patent: May 16, 2006

(54) OVERLAY TARGETS WITH ISOLATED, CRITICAL-DIMENSION FEATURES AND APPARATUS TO MEASURE OVERLAY

(75) Inventor: Abdurrahman Sezginer, Los Gatos, CA (US)

(73) Assignee: Therma-Wave, Inc., Fremont, CA (US)

( * ) Notice: Subject to any disclaimer, the term of this patent is extended or adjusted under 35 U.S.C. 154(b) by 248 days.

(21) Appl. No.: 10/459,631

(22) Filed: Jun. 11, 2003

(65) Prior Publication Data

US 2004/0004726 A1    Jan. 8, 2004

Related U.S. Application Data

(60) Provisional application No. 60/394,201, filed on Jul. 5, 2002.

(51) Int. Cl.
G01B 11/24    (2006.01)
G01B 11/04    (2006.01)

(52) U.S. Cl. .................... 356/601; 356/625; 356/635

(58) Field of Classification Search ........ 356/601–623, 356/399–401, 625–632
See application file for complete search history.

(56) References Cited

U.S. PATENT DOCUMENTS

| | | | |
|---|---|---|---|
| 4,710,642 A | 12/1987 | McNeil | 250/571 |
| 4,999,014 A | 3/1991 | Gold et al. | 356/382 |
| 5,042,951 A | 8/1991 | Gold et al. | 356/369 |
| 5,159,412 A | 10/1992 | Willenborg et al. | 356/445 |
| 5,166,752 A | 11/1992 | Spanier et al. | 356/369 |
| 5,181,080 A | 1/1993 | Fanton et al. | 356/381 |
| 5,412,473 A | 5/1995 | Rosencwaig et al. | 356/351 |
| 5,596,411 A | 1/1997 | Fanton et al. | 356/369 |
| 5,739,909 A | 4/1998 | Blayo et al. | 356/369 |
| 5,867,276 A | 2/1999 | McNeil et al. | 356/445 |
| 5,889,593 A | 3/1999 | Bareket | 356/445 |
| 5,963,329 A | 10/1999 | Conrad et al. | 356/372 |
| 6,278,519 B1 | 8/2001 | Rosencwaig et al. | 356/369 |
| 6,317,211 B1 | 11/2001 | Ausschnitt et al. | 356/401 |
| 6,429,943 B1 | 8/2002 | Opsal et al. | 356/625 |
| 6,813,034 B1 * | 11/2004 | Rosencwaig et al. | 356/601 |
| 6,842,259 B1 * | 1/2005 | Rosencwaig et al. | 356/601 |
| 2002/0135783 A1 * | 9/2002 | Opsal et al. | 356/625 |
| 2002/0158193 A1 | 10/2002 | Sezginer et al. | 250/237 |
| 2004/0046968 A1 * | 3/2004 | Opsal et al. | 356/625 |
| 2005/0057760 A1 * | 3/2005 | Opsal et al. | 356/625 |

FOREIGN PATENT DOCUMENTS

WO    WO 02/25723    3/2002

* cited by examiner

*Primary Examiner*—Hoa Q. Pham
(74) *Attorney, Agent, or Firm*—Stallman & Pollock LLP

(57) ABSTRACT

An optical metrology system is disclosed which is configured to minimize the measurement of specularly reflected light and measure primarily scattered light. The system is similar to prior art beam profile measurements but includes a movable baffle to selectively block specularly reflected light. In addition, certain non-periodic, isolated targets are disclosed suitable for evaluating overlay registration.

13 Claims, 9 Drawing Sheets

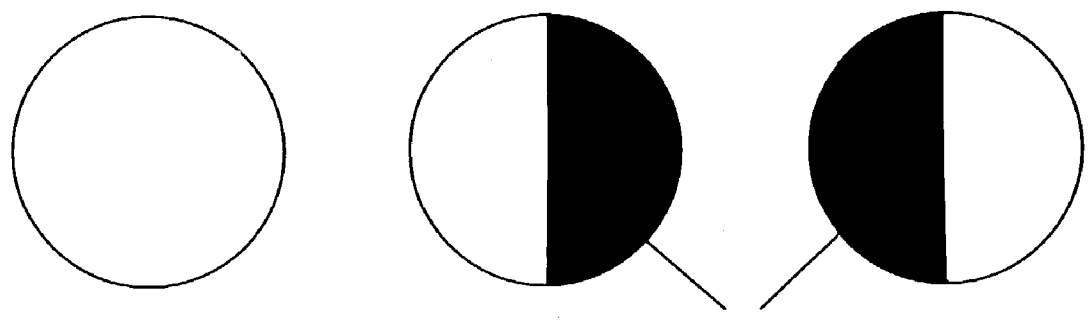
Figure 6 Three states of the movable baffle

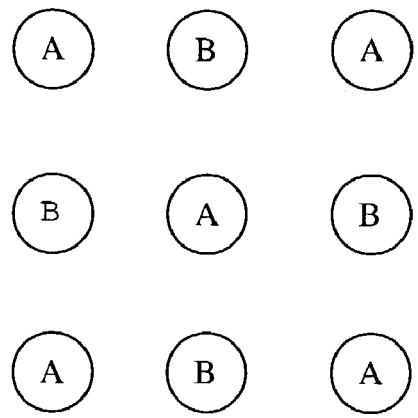
Figure 7 Plan view of overlay target
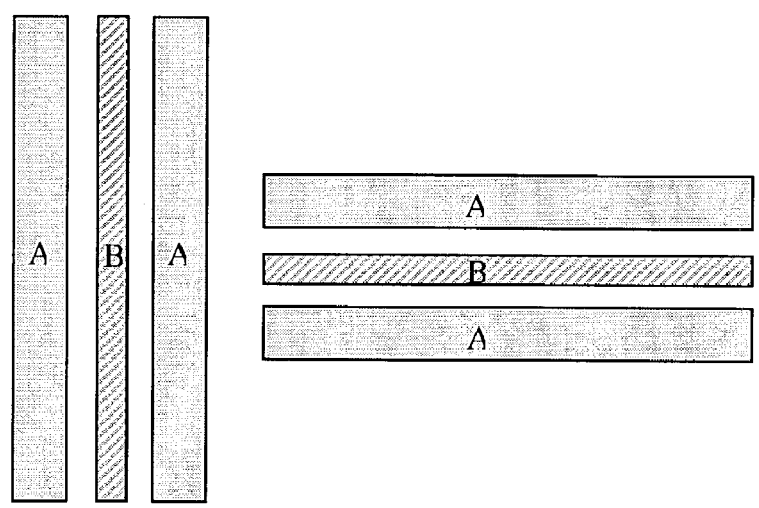
Figure 8 Plan view of X and Y overlay targets for line shaped features

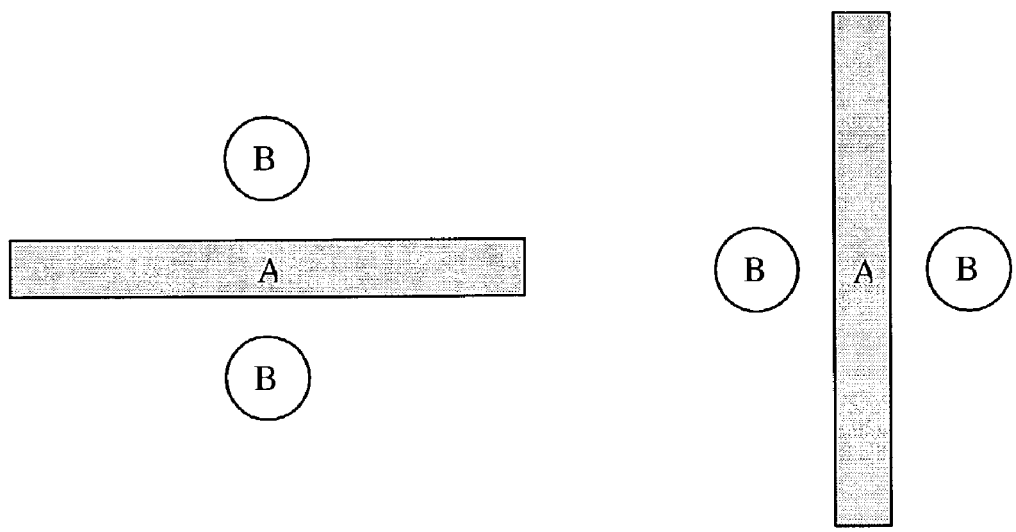
Figure 9 Plan view of X and Y overlay targets for contact holes

OVERLAY TARGETS WITH ISOLATED, CRITICAL-DIMENSION FEATURES AND APPARATUS TO MEASURE OVERLAY

PRIORITY CLAIM

This application claims priority from prior provisional application Ser. No. 60/394,201, filed Jul. 5, 2002, which is incorporated herein by reference.

TECHNICAL FIELD

The subject invention relates to optical metrology equipment for measuring critical dimensions and feature profiles of isolated and aperiodic structures on semiconductor wafers. This invention further relates to measuring the overlay alignment accuracy of a pair of patterned layers on a semiconductor wafer, possibly separated by one or more layers, made by two or more lithography steps during the manufacture of semiconductor devices.

BACKGROUND

There is considerable interest in measuring small geometrical structures formed on semiconductor wafers. These structures correspond to physical features of the device including conductive lines, holes, vias and trenches as well as alignment or overlay registration markings. These features are typically too small to be measured with conventional optical microscopes. Accordingly, optical scatterometry techniques have been developed to address this need.

In a conventional optical scatterometry system, a light beam is directed to reflect off a periodic structure. The periodic structure acts as an optical grating, scattering some of the light. The light reflected from the sample is then measured. Some systems measure light diffracted into one or more higher orders. Other systems measure only the specularly reflected light and then deduce the amount of light scattered into higher orders. In any event, the measurements are analyzed using scattering theory, for example, a Rigorous Coupled Wave Analysis, to determine the geometry of the periodic structure.

Rigorous Coupled Wave Theory and other similar techniques rely upon the assumption that the structure which is being inspected is essentially periodic. To match theory to experiment, the diameter of the light beam spot on the sample is typically significantly larger than individual features on the test structure and encompasses many cycles of the grating. Most prior art systems operate wherein the probe light beam spot overlaps at least twenty repeating patterns so that the diffraction analysis will have statistical significance. The results of the analysis represent an average of the geometry illuminated by the probe beam.

In real world semiconductor devices, many features are isolated or aperiodic. These isolated structures cannot not evaluated with the grating analysis approaches described above. Accordingly, in order to monitor the geometry of isolated features within the dies on the wafer, manufacturers build test structures on the "streets" of "scribe lines" separating the dies. These test structures are periodic but are intended to have the same geometry (e.g. width, shape) as individual features within the die. By measuring the shape of the test structures, one can gain information about the structure in the dies or overlay registration.

This latter approach has been finding acceptance in the industry. Examples of prior art systems which rely on scatterometry techniques can be found in U.S. Pat. Nos. 5,867,276; 5,963,329; and 5,739,909. These patents describe using both spectrophotometry and spectroscopic ellipsometry to analyze periodic structures and are incorporated herein by reference. See also PCT publication WO 02/065545, incorporated herein by reference which describes using scatterometry techniques to perform overlay metrology.

In addition to multiple wavelength measurements, multiple angle measurements have also been disclosed. In such systems, both the detector and sample are rotated in order to obtain measurements at both multiple angles of incidence and multiple angles of reflection. (See, U.S. Pat. No. 4,710,642)

About fifteen years ago, the assignee herein developed and commercialized a multiple angle of incidence measurement system which did not require tilting the sample or moving the optics. This system is now conventionally known as Beam Profile Reflectometry® (BPR®). This and related systems are described in the following U.S. Pat. Nos.: 4,999,014; 5,042,951; 5,181,080; 5,412,473 and 5,596,411, all incorporated herein by reference. The assignee manufactures a commercial device, the Opti-Probe which takes advantage of some of these simultaneous, multiple angle of incidence systems. A summary of all of the metrology devices found in the Opti-Probe can be found in U.S. Pat. No. 6,278,519, incorporated herein by reference.

In the BPR tool, a probe beam from a laser is focused with a strong lens so that the rays within the probe beam strike the sample at multiple angles of incidence. The reflected beam is directed to an array photodetector. The intensity of the reflected beam as a function of radial position within the beam is measured. Each detector element captures not only the specularly reflected light but also the light that has been scattered into that detection angle from all of the incident angles. Thus, the radial positions of the rays in the beam illuminating the detector correspond to different angles of incidence on the sample plus the integrated scattering from all of the angles of incidence contained in the incident beam. The portion of the detector signal related to the specularly reflected light carries information highly influenced by the compositional characteristics of the sample. The portion of the detector signal related to the scattered light carries information influenced more by the physical geometry of the surface.

U.S. Pat. No. 5,042,951 describes an ellipsometric version of the BPR, which, in this disclosure will be referred to as Beam Profile Ellipsometry (BPE). The arrangement of the BPE tool is similar to that described for the BPR tool except that additional polarizers and/or analyzers are provided. In this arrangement, the change in polarization state of the various rays within the probe beam are monitored as a function of angle of incidence. Both the BPR and BPE tools were originally developed for thin film analysis. One advantage of these tools for thin film analysis is that the laser beam could be focused to a small spot size on the sample. In particular, the lens can produce a spot of less than five microns in diameter and preferably on the order of 1 to 2 microns in diameter. This small spot size permitted measurements in very small regions on the semiconductor.

This clear benefit in the thin film measurement field was seen as a detriment in the field of measuring and analyzing gratings with a scatterometry approach. More specifically, a spot size on the order of 1 to 2 microns encompasses less than twenty repeating lines of a conventional test grating. It was believed that such a small sampling of the structure would lead to inaccurate results.

One approach for dealing with this problem was described in U.S. Pat. No. 5,889,593 incorporated herein by reference. This patent describes adding an optical imaging array to the BPR optics which functions to break the coherent light into spatially incoherent light bundles. This forced incoherence produces a much larger spot size, on the order of ten microns in diameter. At this spot size, a suitable number of repeating features will be measured to allow analysis according to a grating theory.

In U.S. Pat. No. 6,429,943 (incorporated by reference), the inventors herein disclosed some alternate approaches for adapting BPR and BPE to measuring periodic gratings. In one approach, the laser probe beam is scanned with respect to the repeating structure to collect sufficient information to analyze the structure as a grating. In another approach, an incoherent light source is used as the probe beam. The incoherent source creates a spot size significantly larger than the laser source and thus could be used to analyze gratings.

Semiconductor manufacturers continually strive to reduce the size of features on a wafer. This size reduction also applies to the width of the streets, typically used as the location for the test structures including overlay registration markings. With narrower streets, the size of the test structures need to be reduced. Ideally, test structures could be developed that were not periodic gratings but closer in form to the actual isolated or aperiodic structures on the dies. Even more desirable would be to develop an approach which would permit measurement of the actual structures within the dies.

With today's small feature sizes, it has been generally believed that direct accurate measurements of isolated or substantially aperiodic structures could not be performed. An isolated structure would correspond to, for example, a single line, trench, hole or via or a specific alignment mark. Such a structure can have extremely small dimensions (i.e., a single line can have a width of about a tenth of a micron).

In order to optically inspect such small structures, a very small illumination spot is desirable. In the broadband applications such as those discussed above, the probe beam spot size is relatively large, on the order of 50 microns in diameter. If this probe beam was focused on an isolated structure, the portion of the measured signal attributable to the isolated structure would be extremely small. Although the spot size of a laser beam is much smaller, it was not envisioned that a enough of a signal could be obtained to measure an isolated feature. Nonetheless, in initial experiments, it has been shown that BPR and BPE techniques using a laser as a probe source can generate meaningful data for isolated structures.

The subject invention also relates to overlay metrology. Overlay metrology is the art of checking the quality of alignment after lithography. Overlay error is defined as the offset between two patterned layers from their ideal relative position. Overlay error is a vector quantity with two components in the plane of the wafer. Perfect overlay and zero overlay error are used synonymously. Depending on the context, overlay error may signify one of the components or the magnitude of the vector.

Overlay metrology provides the information that is necessary to correct the alignment of the stepper-scanner and thereby minimize overlay error on subsequent wafers. Moreover, overlay errors detected on a given wafer after exposing and developing the photoresist can be corrected by removing the photoresist and repeating the lithography step on a corrected stepper-scanner. If the measured error is minor, parameters for subsequent steps of the lithography process could be adjusted based on the overlay metrology to avoid excursions.

BRIEF DESCRIPTION OF THE DRAWING

FIG. 6 is provided to illustrate the results of moving a baffle to different positions.

FIG. 7 is a plan view of one form of overlay target made up of isolated features that simultaneously provide information about X and Y offsets.

FIG. 8 is a plan view of another form of overlay target that includes isolated lines.

FIG. 9 is plan view of another form of overlay target that includes a combination of lines and circular features.

DETAILED DESCRIPTION OF THE PREFERRED EMBODIMENTS

Figure 1:
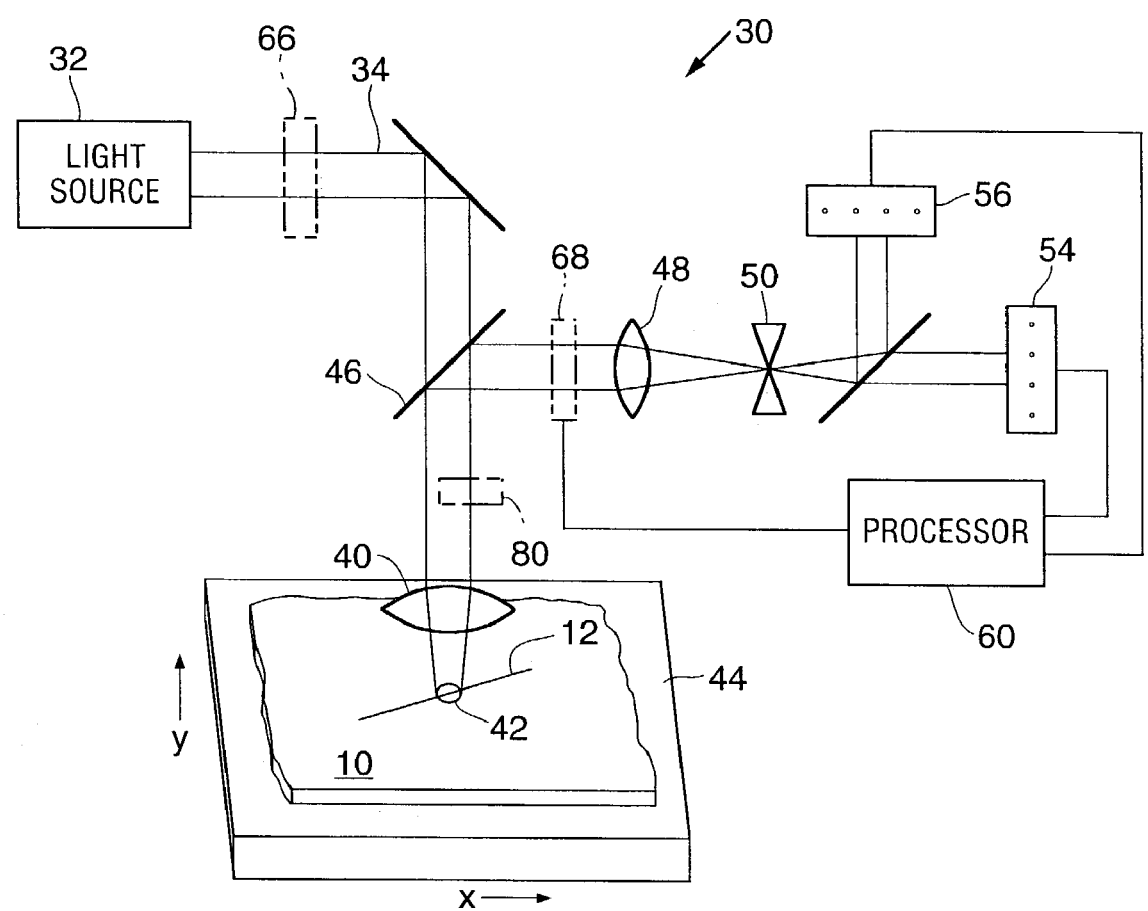
FIG. 1 is a schematic diagram of an apparatus for performing the method of the subject invention.

Turning to FIG. 1, a basic schematic diagram of a simultaneous multiple angle of incidence apparatus 30 is illustrated. Further details about such a device are described in U.S. Pat. Nos. 4,999,014; 5,042,951; 5,159,412; 5,412,473 and 6,429,943, all incorporated herein by reference. As noted above, the assignee's Opti-Probe device incorporates portions of this technology and markets the measurement subsystem under the trademarks Beam Profile Reflectometry or BPR (as well as a Beam Profile Ellipsometry (BPE) variant described in U.S. Pat. No. 5,181,080). In the past, the BPR and BPE technologies were utilized primarily to analyze the characteristics of thin films and, very recently, periodic grating structures formed on semiconductors. This disclosure is directed to using the measurements which can be obtained from this type of system to evaluate the geometry of isolated features and aperiodic structures formed on semiconductors.

The basic measurement system includes a light source 32 for generating a probe beam 34. To carry out this method, the light source should be a laser for generating a coherent beam of radiation. Laser diodes are suitable laser sources for this application. If the output of the laser is not itself polarized, a separate linear polarizer can be provided. The laser output can be coupled to a fiber delivery system as described in PCT WO 01/55671.

The probe beam 34 is focused onto the feature 12 on the sample 10 using a lens 40 in a manner so that the rays within the probe beam create a spread of angles of incidence. The sample is shown supported by a stage 44. In the preferred embodiment, the beam is directed normal to the surface of the sample but can be arranged off-axis as illustrated in U.S. Pat. No. 5,166,752, incorporated by reference. Lens 40 can be a high numerical aperture lens (on the order of 0.90 NA) to create angles of incidence from zero to about 70 degrees.

A lens having an NA of at least 0.5 is preferred. A total range of angles of incidence of at least thirty degrees is also preferred. The lens creates rays having predominantly S-polarized light along one axis and predominantly P-polarized light along an orthogonal axis. At intermediate angles, the polarization is mixed.

In certain measurement situations, it may be desirable to have the probe beam 34 underfill lens 40 resulting in a lower effective numerical aperture. For example, the beam may be configured so that the effective numerical aperture is 0.5 which would create a spread of angles of incidence from zero to about 30 degrees. The actual larger NA of the lens (0.9) would be beneficial in collecting a larger portion of the reflected and scattered light.

Lens 40 is positioned to create a probe beam spot 42 on the sample. When using a high numerical aperture lens (0.9) that is overfilled by the probe beam, a spot size having a diameter as small as two microns or less can be achieved. If a lens with a smaller NA is used, the spot size would typically be larger. In most measurements situations, it would appear desirable to have the spot size less than five microns in diameter. However, in the situation discussed above, where the lens is underfilled, the spot size could be larger than five microns.

Light reflected by the feature (both specular and scattered) is collected by the lens 40 and collimated. The reflected light is redirected by a splitter 46 to an imaging lens 48. Lens 48 magnifies and relays an image of the sample at the focal plane of the lens. A spatial filter 50 having an aperture is placed in the focal plane of the lens 48 for controlling size of the area of the sample which is measured.

The probe beam is then passed through a 50—50 splitter and directed to two photodetectors 54 and 56 having a linear array of detector elements. The photodetectors are arranged orthogonal to each other to measure both the S and P polarization components. As described in detail in the above-cited patents, each of the detecting elements in the array measures light specularly reflected from different angles of incidence. The radial position within the reflected probe beam is mapped to the angle of incidence, with the rays closer to the center of the beam having the smallest angles of incidence and the rays in the radially outer portion of the beam corresponding to the greatest angles of incidence. Thus, each detector element simultaneously generates an independent signal that correspond to a different angle of incidence on the sample plus the integrated scattering from all of the angles of incidence contained in the incident beam.

The output signals from the detector arrays are supplied to the processor 60. Processor 60 will analyze the signals based on algorithms that consider the reflected and scattered light. The algorithms rely on the Fresnel equations. As noted above, since the structure is not periodic, Rigorous Coupled Wave Theory would not be well suited to the analysis. Rather, and as discussed below, boundary or-volume integral approaches, are better suited to this problem.

The selected algorithms will correlate the variation in reflectivity as a function of the position on the detector with the geometry of the aperiodic structure. The type of analysis will depend on the application. For example, when used for process control, either in situ or near real time, the processor can compare the detected signals to an expected set of signals corresponding to the desired geometry of the aperiodic structure. If the detected signals do not match the expected signals, it is an indication that the process is not falling within the specified tolerances and should be terminated and investigated. In this approach, no sophisticated real time analysis of the signals is necessary.

The reflected output signals can be more rigorously analyzed to determine the specific geometry of the aperiodic structure. While there are a number of different approaches, most have certain traits in common. More specifically, the analytical approach will typically start with a theoretical "best guess" of the geometry of the measured structure. Using Fresnel equations covering both the reflection and scattering of light, calculations are applied to a theoretical model of the structure to determine what the expected measured output signals would be for the theoretical geometry. These theoretical output signals are compared to the actual measured output signals and the differences noted. Based on the differences, the processor will generate a new set of theoretical output signals corresponding to a different theoretical structure. Another comparison is made to determine if the theoretical signals are closer to the actual measured signals. These generation and comparison steps are repeated until the differences between the theoretically generated data and the actually measured data are substantially minimized. Once the differences have been minimized, the theoretical structure corresponding to the best fit theoretical data is assumed to represent the actual structure.

This minimization procedure can be carried out with a conventional least squares fitting routine such as a Levenberg-Marquardt algorithm. It would also be possible to use a genetic algorithm. (See, U.S. Pat. No. 5,953,446.)

Ideally, the minimization routine will be carried out in real time, associated with the measurements. Since the calculations related to this analysis are very complex, real time calculations can be a challenge. Some approaches for dealing with complex real time calculations are set forth in our co-pending U.S. patent application Ser. No. 09/906,290, filed Jul. 16, 2001, incorporated herein by reference.

Another approach to dealing with the processing difficulties is to create a library of solutions prior to the measurement. In this approach, a range of possible structures and their associated theoretical output signals are generated in advance. The results are stored as a library in a processor memory. During the measurement activities, the actual measured signals are compared with sets of theoretically generated output signals stored in the library. The structure associated with the set of theoretical signals which most closely matches the actual measured data is assumed to most closely represent the geometry of the measured structure. The use of libraries is disclosed in U.S. patent application 2002/0035455 A1. Still another approach is to create a much smaller database of possible solutions. Measured data can then be compared to the database and algorithms are used to interpolate between data points to derive a solution to the geometry of the structure. (See for example, U.S. patent application 2002/0038196 A1)

Theory

As noted above, an isolated feature should not be modeled in the same manner as a diffraction grating. We have addressed the issue with two different approaches. The first approach uses Fourier expansions which are analogous in many ways to the Rigorous Coupled Wave Theory. We have also developed an analysis using a boundary integral approach. Previously we have developed a boundary integral approach for periodic gratings using Green's functions. This work is described in U.S. patent application Ser. No. 10/212,385, filed Aug. 5, 2002 and incorporated herein by reference. Another suitable analytical approach includes a finite difference analysis as described in U.S. patent application Ser. No. 10/345,814, filed Jan. 16, 2003 and incorporated herein by reference We have found that the analysis by Fourier expansion tends to be faster than the boundary integral approach. Fourier expansion is relatively easy to implement since it is similar to the periodic case. However, the Fourier expansion approach is less stable. Further, there are more control parameters one has to adjust, including the number of integration points in the exterior and interior regions, and the cutoff integration parameter $s_0$. The boundary integral approach is more numerically involved and is more difficult to implement. However, it is more robust. We have used both approaches to evaluate isolated lines with single material in the line. The results of both approaches agree very well, indicating that our results are valid.

Fourier Expansions

An isolated or aperiodic feature (e.g. single line or trench) can be viewed as an array of lines or trenches with very large periods. Thus, in an approach which is analogous to the RCWA theory of the diffraction gratings, we can write the electric field as $$E(x,z) = \int dk E(k,z)e^{ikx} = k_0 \int ds E(\sin\theta, z)e^{ik_0 sx}$$
$$\approx k_0 \sum_j w_j f(s_j, z)e^{ik_0 s_j x}$$

where s is the equivalent of $\sin\theta$, the $s_j$ are the Guassian quadrature nodes, in contrast to the periodic systems where $s_j$ are equally spaced, the $w_j$ are the weights. The input electric field is written as $$E_0 = k_0 \int_{-s_0}^{s_0} ds E_0(s,z)e^{ik_0 sx}$$

where $s_0 \leq 1$. In general, the electric field as a function of s is not analytic, therefore we need to perform the integration in at least 3 regions, $(-\infty,-1),(-1,1),(1,\infty)$. Furthermore, we need to have a cutoff $s_{max}$ for s so that in each region we can use Gaussian quadrature for the integrations. For TM mode, we use the equivalent of TM1 implementation.

Boundary Integral Approach

As noted above, although a Fourier expansion approach can be used, boundary or volume integral methods are ideal for isolated features in that they provide a more robust solution. The boundary integral formulation relies on the Green's theorem, the properties of the wave function and Green's functions.

For the isolated feature situation, the equation of motion for the TE mode is $$\Delta\psi(x)-\epsilon(x)\psi(x)=0,$$

$$\Delta G(x,x')-\epsilon(x)G(x,x')=\delta(x-x').$$

and Green's theorem states that $$\int dV\psi(x)\delta(x-x') = \int dV[\psi(x)\Delta G(x,x') - \Delta\psi(x)G(x,x')] =$$

-continued $$\begin{cases} \psi(x'), & x' \ \varepsilon \ V \\ \frac{1}{2}\psi(x'), & x' \ \varepsilon \ \Gamma \\ 0, & x' \ \varepsilon \ V \end{cases} = \int d\Gamma[\psi(x)\partial_n G(x,x') - \partial_n \psi(x) G(x,x')].$$

where $\Gamma$ represents the boundary of the region of interest. In our case, it is simply a curve since the y dimension is of no concern. Since the boundary conditions require that $\psi(x)$, $G(x,x')$, $\partial_n\psi(x)$, and $\partial_n G(x,x')$ be continuous across material boundaries, the volume can be extended over several materials provided that G is obtained.

For TM mode, $$\nabla\epsilon^{-1}\nabla\psi(x)-\psi(x)=0$$

$$\nabla\epsilon^{-1}\nabla G(x,x')-G(x,x')=\delta(x,x').$$

We use modified Green's theorem $$\int dV\psi(x)\delta(x-x') = \int dV[\psi(x)\nabla\epsilon^{-1}\nabla G(x,x') - \nabla\epsilon^{-1}\nabla\psi(x)G(x,x')] =$$

$$\begin{cases} \psi(x'), & x' \ \varepsilon \ V \\ \frac{1}{2}\psi(x') & x' \ \varepsilon \ \Gamma \\ 0 & x' \ \varepsilon \ V \end{cases} = \int d\Gamma\epsilon^{-1}[\psi(x)\partial_n G(x,x') - \partial_n \psi(x)G(x,x')].$$

Since the boundary conditions are $\psi(x)$, $G(x,x')$, $\epsilon^{-1}\partial_n\psi(x)$, and $\epsilon^{-1}\partial_n G(x,x')$ and a continuous, the integration is again meaningful over different material domains. We write the total field in the exterior region as a combination of incident field and scattered field $$\psi(X)=\psi_0(X)+\psi_s(X),$$

If X' is in the exterior region, we have $$\int d\Gamma n \cdot [\psi(X)\nabla G(X,X') - \nabla\psi(X)G(X,X')] =$$

$$\int d\Gamma_\infty n \cdot [\psi(X)\nabla G(X,X') - \nabla\psi(X)G(X,X')] +$$

$$\int d\Gamma_0 n \cdot [\psi(X)\nabla G(X,X') - \nabla\psi(X)G(X,X')] =$$

$$\int d\Gamma_\infty n \cdot [\psi_0(X)\nabla G(X,X') - \nabla\psi_0(X)G(X,X')] +$$

$$\int d\Gamma_0 n \cdot [\psi_s(X)\nabla G(X,X') - \nabla\psi_s(X)G(X,X')] =$$

$$\psi_0(X') + \int d\Gamma_0 n \cdot [\psi_s(X)\nabla G(X,X') - \nabla\psi_s(X)G(X,X')]$$

When X' is on the boundary $\Gamma_0$, we have $$\int d\Gamma n \cdot [\psi(X)\nabla G(X,X') - \nabla\psi(X)G(X,X')] =$$

$$\psi_0(X') + \int d\Gamma_0 n \cdot [\psi(X)\nabla G(X,X') - \nabla\psi(X)G(X,X')]\frac{1}{2}\psi(X') =$$

$$\psi_0(X') - \int d\Gamma_0 n \cdot [\psi(X)\nabla G(X,X') - \nabla\psi(X)G(X,X')]$$

While in interior region, we have $$\frac{1}{2}\psi(X') = \int d\Gamma'_0 n \cdot [\psi(X)\nabla G'(X, X') - \nabla\psi(X)G'(X, X')]$$

Combine the two we have $$\frac{1}{2}\psi(X') + \int d\Gamma'_0 n \cdot [\psi(X)\nabla G_{ext}(X, X') - \nabla\psi(X)G_{ext}(X, X')] = \psi_0(X')$$

$$\frac{1}{2}\psi(X') - \int d\Gamma'_0 n \cdot [\psi(X)\nabla G_{int}(X, X') - \nabla\psi(X)G_{int}(X, X')] = 0$$

When these last two equations are discretized either with boundary element or quadrature method, they become a set of linear equations which can be solved directly if the dimensions are relatively small or iteratively if the system is large.

We have performed initial testing using the subject method to measure an isolated trench formed on a semiconductor wafer. The wafer was silicon with a 650 nm top layer of silicon dioxide. The isolated trench had a nominal width of about 500 nanometers (0.5 microns) and a nominal depth of about 650 nanometers. A beam profile reflectometer of the type illustrated in FIG. 1 and found in the assignee's Opti-Probe system was used to measure the sample. The photodetector arrays in this system generate output signals corresponding to angles of incidence ranging from about +70 degrees to −70 degrees around the normal to the sample.

Figure 2:
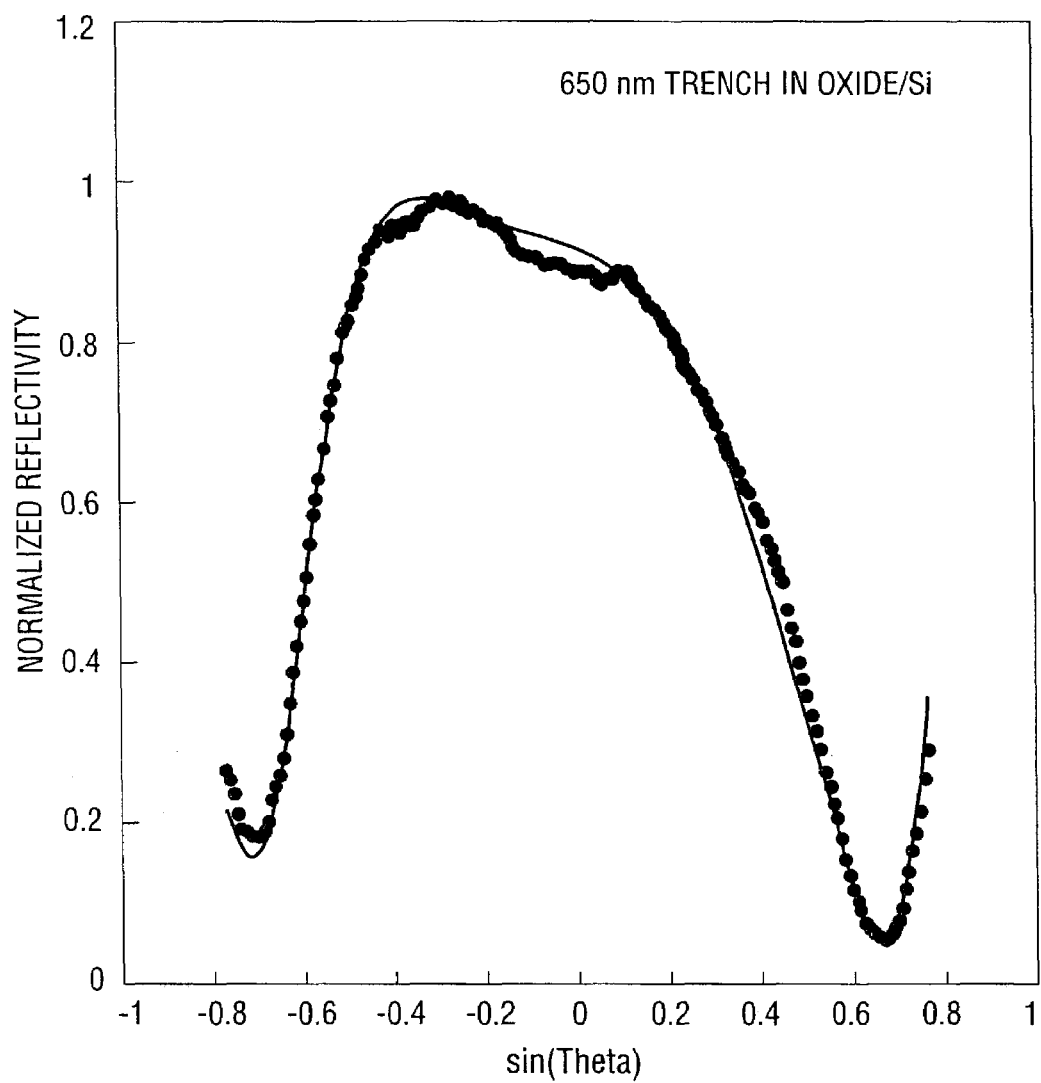
FIG. 2 is a graph of normalized reflectivity as a function of angle of incidence and comparing actual measured data to predicted data associated with an isolated trench.
Figure 3:
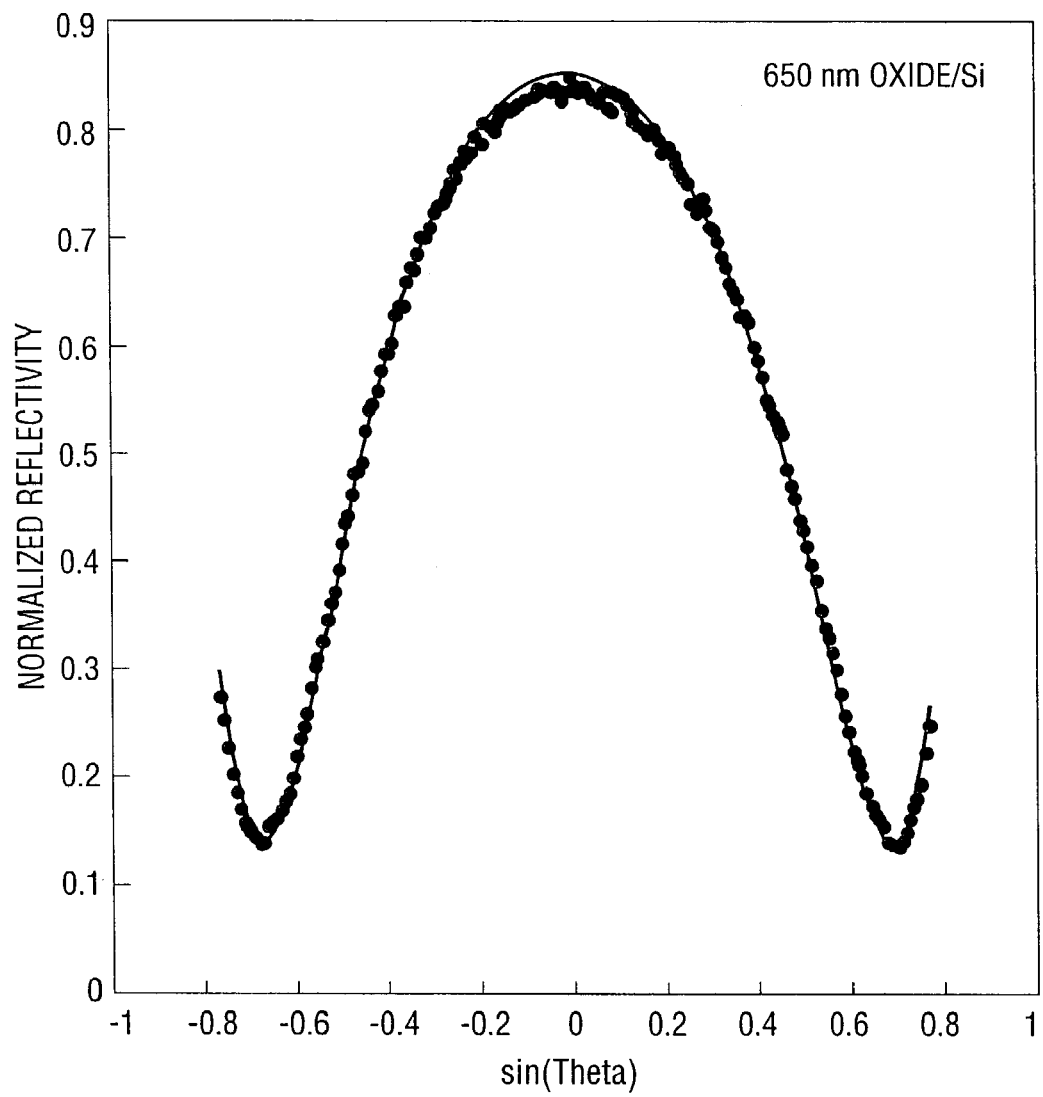
FIG. 3 is a graph of normalized reflectivity as a function of angle of incidence and comparing actual measured data to predicted data associated with an unpatterned thin film.

FIGS. 2 and 3 illustrate measurements made on the sample wafer. FIG. 2 illustrates measurements with the probe beam over the trench while FIG. 3 illustrates measurements with the probe beam positioned on an unpatterned portion of the wafer. In each Figure, the circles represent actual measurements plotted as a function of angle of incidence. The smooth lines represent a theoretical fit of the data.

Figure 4:
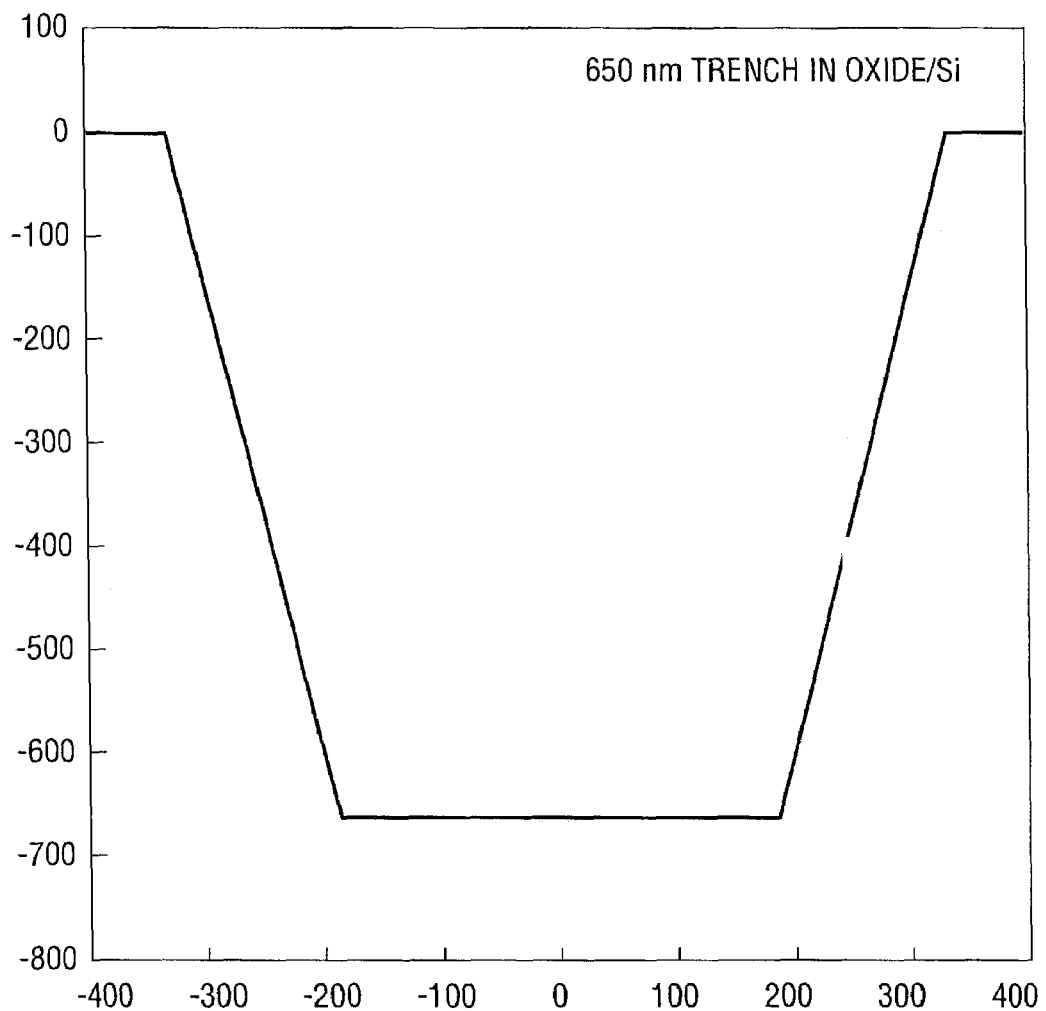
FIG. 4 is a cross-section shape of a trench predicted by an analysis of the measured data illustrated in FIG. 2.

The differences between the data in FIGS. 2 and 3 illustrate that a single narrow trench in the field of view effects the BPR measurement. The parameters used to create the solid line in FIG. 2 are based on a trench having dimensions illustrated in FIG. 4. These initial experiments fully demonstrate the feasibility of using BPR to measure a small, isolated, aperiodic feature on a semiconductor sample.

The subject invention is not limited specifically to the BPR arrangement illustrated above. For example, various other forms of detector arrays can be used. In particular, it is feasible to replace one or both of the arrays with a two dimensional array such as a CCD. Those skilled in the art will readily be able to envision other modifications, including those described in the patent documents cited herein.

Embodiment for Minimizing Specular Light Detection

As noted above, the output of the detector elements includes both a specularly reflected component and a scattered light component. It may be desirable to minimize the specularly reflected component and maximize the scattered light component. This can be important if the primary interest is in characterizing the physical structure of the scatterer and less information is needed about the underlying structure.

One approach for achieving the latter goal is described in copending provisional application Ser. No. 60/394,201 filed Jul. 5, 2002, assigned to the same assignee herein and incorporated by reference. This disclosure proposes inserting a baffle 80 (shown in phantom in FIG. 1) into a portion of the probe beam path. The baffle is intended to block a semi-circular portion of the probe beam. In this arrangement, light in the left hand portion of the incident beam reaches the sample while light in the right hand portion of the incident beam is blocked. Specularly reflected light is collected by the right hand side of lens 40 but is blocked from reaching the detector by baffle 80. In contrast, only light which has been scattered from the sample and captured by the left hand side of the lens will reach the detector. In this manner, the light reaching the detector will be primarily scattered light and not specularly reflected light. Additional measurements can be taken after moving the baffle to block the left hand side of the incident beam.

As can be appreciated, with a baffle in place, the output generated by the detectors does not correspond to specific incidence angles as in a conventional BPR arrangement. Rather, the detectors measure an integration of scattered light from various angles of incidence.

A measurement system including a baffle in the manner describe above can be used to measure scattered light from both isolated structures as well as periodic structures. Such a baffle structure can be used to analyze overlay registration as discussed below.

Figure 5A:
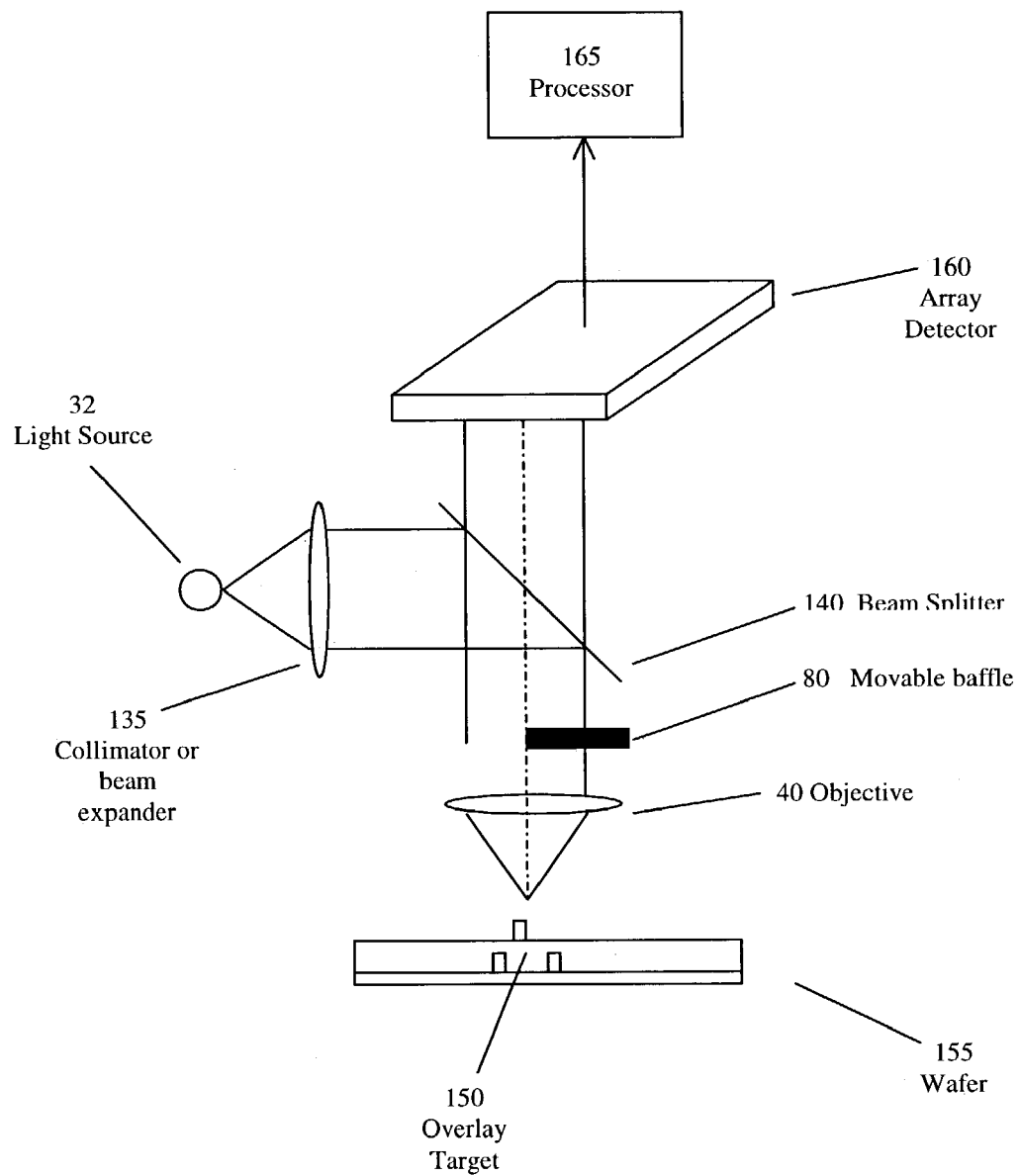
FIG. 5a is a schematic diagram of a first embodiment of an apparatus arranged to measure overlay registration.

The application of the system that includes a baffle to measure overlay registration is illustrated in FIG. 5*a*. FIG. 5*a* is similar to FIG. 1 with like numbers corresponding to like parts. As seen therein, a light 32 is collimated by collimator 135 and reflected by a beam splitter 140. The light source 32 can be monochromatic. The wavelength of the light source 32 can be variable. In one implementation, the light source 32 is a bank of lasers or a laser with multiple emission lines or a tunable laser. Alternatively, light source 32 can be the output of a broadband light source coupled to a monochrometer.

The light that is reflected off the beam splitter 140 is focused by the objective 40 onto the overlay target 150 on the wafer 155 under test. The light that is reflected and scattered by the overlay target is mapped onto an array detector 160. Detector 160 is a 2-dimensional array such as a CCD.

Movable baffle 80 has three states shown in FIG. 6: open, blocking half of the aperture, blocking the other half of the aperture. The baffle can be a dark sheet that is moved mechanically. Alternatively, the baffle can be a two-segment, liquid crystal neumatic or ferroelectric shutter. The output of detector array 160 is recorded in each of the three states of the baffle, for each wavelength. The detector only measures the scattered light when the baffle is inserted. The baffle blocks the specular reflection. The reason for blocking the specular reflection and measuring the scattered light in isolation is that the specular reflection can dominate the total light intensity and may contain little information about isolated small features that make up the target. The purpose of taking a measurement with the baffle fully open is to gather information about the film stack in which the isolated target is embedded. Knowledge of the film stack is necessary for interpreting the scattering of the electromagnetic waves. In an alternative implementation, when the baffle is fully open, the objective moves laterally so that the measurement spot misses the target but looks at the film stack.

FIG. 6 illustrates the baffle covering either the left or right hand side of the aperture corresponding to movement along an axis parallel to the page in FIG. 5. Additional information could be obtained by making additional analogous measurements along an axis perpendicular to the page of FIG. 5 (which would correspond to an illustration in FIG. 6 where the baffle covered either the top or bottom half of the aperture). Taking measurements with the baffle in different positions may aid in evaluating asymmetries of the features.

When the baffle is open, the instrument is similar to Beam Profiling Reflectometer (BPR). (See U.S. Pat. Nos. 4,999,014 and 5,042,951, incorporated herein by reference.) A particular location on the array detector 160 corresponds to a particular angle of incidence on the target. The recorded light intensity depends on the stack of materials on the wafer as well as the features that make up the target. When the baffle partially blocks the aperture, the measured field strongly depends on the features on the target including overlay but also on the stack of materials on the wafer. The fields acquired by detector array 160 for multiple states of the baffle 60 and multiple wavelengths are processed to obtain the parameters of the film stack and the target. The parameters of the target are quantities such as feature thickness, linewidth or diameter, sidewall angle and overlay offset.

Figure 5B:
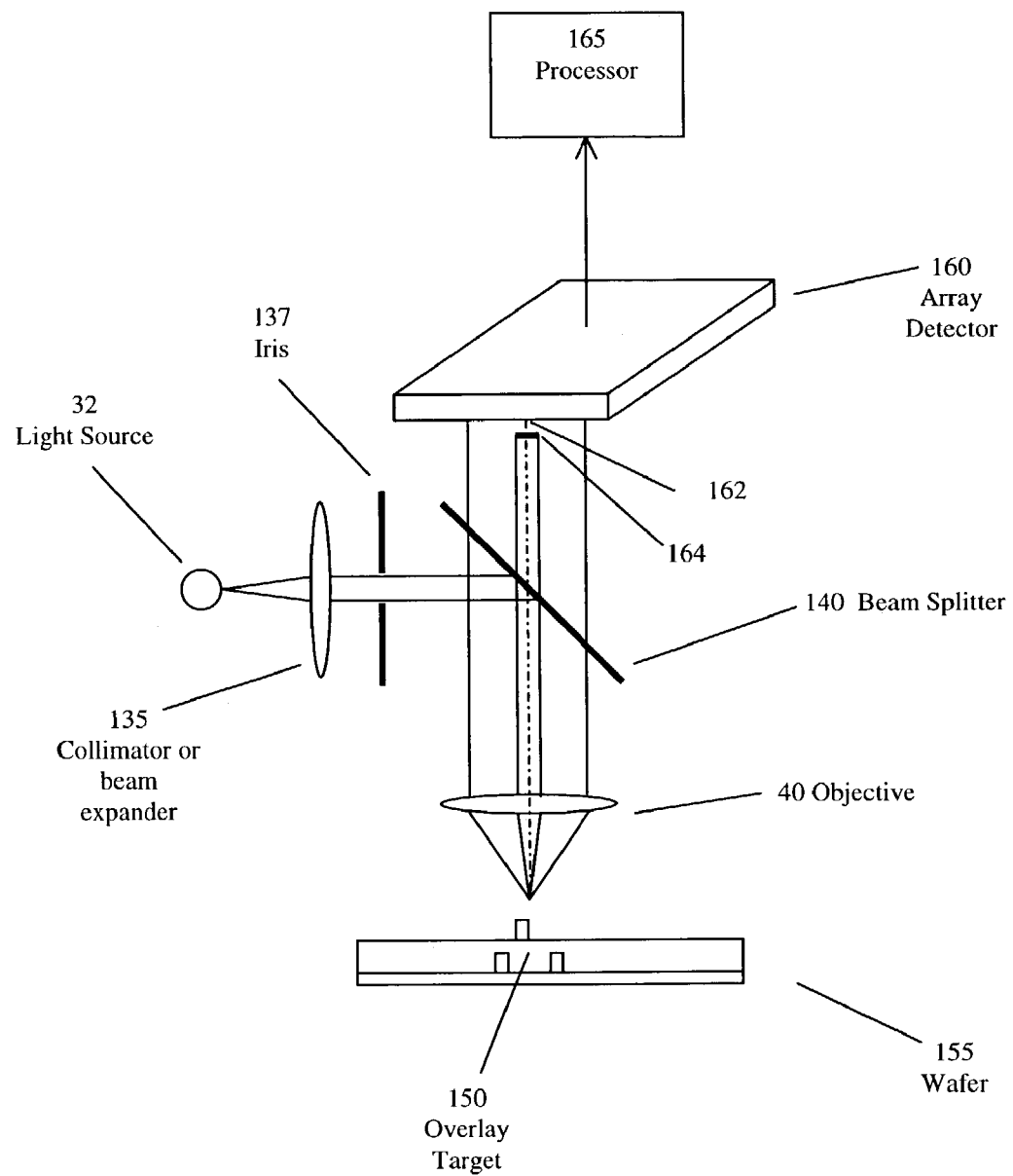
FIG. 5b is a schematic diagram of a second embodiment of an apparatus arranged to measure overlay registration.

An alternative embodiment is shown in FIG. 5b. The numerical aperture of the illumination is substantially smaller than the numerical aperture of detection. This enlarges the illumination spot and possibly makes it larger than the extent of the overlay target 150. The aperture of illumination is controlled by the collimator or beam expander 135, or optionally by iris 137. The specular illumination hits a small portion 162 of the detector array 160. The outputs of pixels in the specular region 162 of detector array 160 are ignored. These pixels are optionally blocked by a baffle 164 to prevent blooming of the detector array. The rest of the detector array 160 measures diffracted light. If the illumination overfills the target, the target is surrounded by an unpatterned film stack.

The general processing steps used to analyze the measured signals will be similar to those discussed above. A model is seeded with an initial guess of target parameters. A calculation is made to predict the electromagnetic wave scattering. The theoretical results are compared to the measured results. The parameters of the target are changed until the difference of the measured and calculated fields are sufficiently close. One preferred search algorithm picks an initial point by comparing the measured field to a database of previously calculated fields. In the second stage, the algorithm uses a minimization algorithm such as the Levenberg-Marquardt algorithm. The model calculation in the Levenberg-Marquardt algorithm can either interpolate the previously calculated database of fields, or solve Maxwell's Equations as needed.

Overlay Targets

FIGS. 7, 8 and 9 illustrate targets that can be used to evaluate overlay registration that do not rely on grating structures. In these Figures, features labeled A are at level A and features labeled B are at level B.

FIG. 7 illustrates a single target grid which would provide information about overlay registration in both X and Y directions simultaneously. More specifically, any overlay error in either direction will vary the scattered light pattern created by this structure.

While the target grid of FIG. 7 theoretically can be used to analyze overlay error, it may be difficult to isolate the changes induced by the error in the X direction from the error in the Y direction. FIGS. 8 and 9 illustrate targets where the errors in the X and Y direction may be more easily decoupled. When using a target as shown in FIG. 8, it may be desirable to scan the probe beam in a direction perpendicular to the lines. This approach would require a scan along the X axis for the three line structure illustrated in the left-hand side of FIG. 8 and a scan along the Y axis for the three line structure illustrated in the right-hand side of FIG. 8. The structure of FIG. 9 mimics contacts (vias) and interconnections in a Damacene process. The spacing and size of the features are the same as in the actual device. This ensures that the metrology target and the devices are subject to the same aberrations of the lithography projector.

The present invention differs from the prior art approaches that use imaging to evaluate overlay in that no attempt is made to form a sharply resolved image of the test target. The features of the target are preferably as small as the critical dimensions of the devices. Such small features cannot be imaged by visible-light optical microscopy. The present invention does not use spatially periodic targets. The targets are not diffraction gratings.

One advantage of the present approach is that the isolated targets are smaller than the ones used in prior art. Further, the critical dimensions of the overlay target and the actual devices on the wafer can be the same. Therefore, lens aberrations of the stepper/scanner affect the overlay targets and devices similarly. In addition, overlay measurements using spatially periodic targets are ambiguous up to an arbitrary multiple of the period. The measurement described here is not ambiguous by a period because it does not use periodic structures.

It should be noted that the targets illustrated in FIGS. 7 to 9 might be usable with many other prior art optical metrology systems. For example, these targets might be measured with an ellipsometer (spectroscopic or otherwise) or a beam profile reflectometer (BPR) without baffle 80, or beam profiling ellipsometer (BPE), a spectroscopic reflectometer, or a variable angle reflectometer or ellipsometer. The optical instrument can be any instrument that measures properties of light that has interacted with the overlay target as a function of one or more of the independent variables: wavelength, polar angle of incidence, azimuthal angle of incidence, polarization states of the incident and detected light.

The data can be processed by a neural-network which is trained previous to the measurements. The neural network can be trained on a set of calculated or measured fields corresponding to known target parameters.

Alternatively, the data can be processed by looking up the measured field in a library of previously computed or measured library of fields. The look-up is performed by finding the library entry whose difference from the measured field has the least variance from the norm.

Alternative Isolated Feature Measurements

The subject methods are not limited to reflectometry. As noted in U.S. Pat. Nos. 5,042,951 and 5,166,752 (incorporated herein by reference), it is also possible to obtain ellipsometric measurements corresponding to $\psi$ and $\Delta$ simultaneously at multiple angles of incidence. To obtain such measurements, some additional optical elements should be added to the device of FIG. 1 (or FIG. 5). For example, a polarizer 66 (shown in phantom) is desirable to accurately predetermine the polarization state of the probe beam. On the detection side, an analyzer 68 (also shown in phantom) is provided to aid in analyzing the change in polarization state of the probe beam due to interaction with the sample. The optical components of the analyzer can be of any type typically used in an ellipsometer such as a polarizer or a retarder. The ellipsometric output signals are analyzed in a fashion similar to the prior art approaches for using ellipsometric data to evaluate the geometry of an aperiodic structures.

U.S. Pat. No. 5,181,080 describes a variant of the BPE approach. In this system, a quadrant detector is used to measure the power of the reflected probe beam along two orthogonal axes. Each quadrant generates a response proportional to the integration of all angles of incidence. By manipulating the output of the quadrants, ellipsometric information can be derived.

It is also within the scope of the subject invention to combine the BPR and BPE measurements with other measurements that might be available from a composite tool. As noted above, the assignee's Opti-Probe device has multiple measurement technologies in addition to the Beam Profile Reflectometry system. These other technologies include broadband reflectometry and broadband ellipsometry. In these measurement technologies, an incoherent polychromatic probe beam is focused onto the sample. The reflected polychromatic probe beam is monitored at a plurality of wavelengths. In reflectometry, changes in intensity of the polychromatic probe beam are monitored. In ellipsometry, changes in polarization state of the polychromatic probe beam are monitored. The output from these additional modules might be useable in combination with the BPR and BPE signals to more accurately evaluate the geometry of the isolated structure.

As can be appreciated, most of the basic hardware elements discussed herein have been known in the prior art. The developments intended to be covered by this disclosure relate to certain applications of that technology. More specifically, it is believed that the BPR and BPE techniques can be used to measure isolated, single (non-repeating) structures which have dimensions in the micron and sub-micron range. These would include, for example, single lines, single vias, single holes and single trenches. It is believed that by focusing a coherent probe beam on the structure and measuring the reflected response, one can rely on scattered light effects to determine the geometry of the structure.

It may also be possible to evaluate a single structure that was larger than the probe beam spot (i.e., was only partially illuminated). By measuring scattered light effects, and with some a priori knowledge of the structure, one may be able to determine the geometry of the structure which is being illuminated.

The subject invention is also intended to cover the situation where a periodic structure has a size or extent smaller than the probe beam spot. For example, consider a repeating structure having only five or ten lines. If the probe beam spot is greater than the structure, the reflected field would be aperiodic and could not be analyzed with a grating approach. However, using the techniques described herein one could still derive information about the sample. In this case, it is assumed that the probe beam spot size would be at least about twice the width of the structure so the grating effects would be minimal.

Although initial experiments have shown that isolated and aperiodic structures can be monitored with the probe beam spatially fixed with respect to the feature, it is within the scope of the subject invention to scan the probe beam with respect to the feature. In such a case, measurements are taken at various positions of the probe beam and the data combined to analyze the sample. Such an approach may be particularly useful with a system operating in accordance with U.S. Pat. No. 5,181,080, discussed above. The relative motion of the probe beam with respect to the sample can be achieved using a conventional motion stage. It is also possible to move the optics. (See for example, PCT WO 00/57127.)

While the subject invention has been described with reference to a preferred embodiment, various changes and modifications could be made therein, by one skilled in the art, without varying from the scope and spirit of the subject invention as defined by the appended claims.

We claim:

1. A method for evaluating the geometry of a structure formed on a sample, said method comprising the steps of:
   generating a probe beam of radiation;
   focusing the probe beam onto the structure with an optical element to create a spread of angles of incidence;
   monitoring the light from the probe beam diffracted from the structure with an array of photodetecting elements and generating output signals in response thereto;
   inserting a baffle across a portion of the beam path in front of the optical focusing element in a manner to increase the amount of scattered light being monitored in comparison to the amount of specularly reflected light being monitored; and
   evaluating the geometry of the structure based on the output signals.

2. A method as recited in claim 1, further including the step of moving the baffle to a second position so that the probe beam can illuminate the structure from a different direction.

3. A method as recited in claim 1, where one aspect of the geometry that is evaluated is the overlay of two patterned layers.

4. A method as recited in claim 1, where one aspect of the geometry that is evaluated is the width and profile of lines.

5. A method as recited in claim 1, where one aspect of the geometry that is evaluated is the depth, diameter, eccentricity, and profile of contact holes.

6. A method as recited in claim 1, where one aspect of the geometry that is evaluated is the height, diameter, eccentricity, and profile of posts.

7. A method as recited in claim 1 wherein the baffle blocks an asymmetrical portion of the beam.

8. An apparatus for evaluating the geometry of a structure formed on a sample, comprising:
   a light source for generating a probe beam of radiation;
   a lens for focusing the probe beam onto the structure to create a spread of angles of incidence;
   a detector having an array of photodetecting elements for measuring the light diffracted from the structure and generating output signals in response thereto;
   a baffle positioned across a portion of the beam path in front of the lens in a manner to increase the amount of scattered light being monitored in comparison to the amount of specularly reflected light from being monitored; and
   a processor for evaluating the geometry of the structure based on the output signals.

9. An apparatus as recited in claim 8, wherein said baffle is movable to a second position so that the probe beam can illuminate the structure from a different direction.

10. An apparatus as recited in claim 8 wherein the baffle blocks an asymmetrical portion of the beam.

11. An apparatus for evaluating the geometry of a structure formed on a sample, comprising:
    a light source for generating a probe beam of radiation;
    a lens for focusing the probe beam onto the structure;

means for restricting the light transmitted by the lens so the numerical aperture of illumination is less than the numerical aperture of detection;

a detector having an array of photodetecting elements for measuring the light diffracted from the structure and generating output signals in response thereto; and a processor for evaluating the geometry of the structure based on the output signals and wherein the information that would be attributed to specular reflection are suppressed such that the amount of scattered light being monitored is increased in comparison to the amount of specularly reflected light being monitored.

12. An apparatus as recited in claim 11, wherein the information that would be attributed to specular reflection are suppressed by ignoring signals in the region of the detector which map to the specularly reflected light.

13. An apparatus as recited in claim 11, wherein the information that would be attributed to specular reflection are suppressed by blocking the light attributed to the specularly reflected light from reaching the detector with a blocking member.

* * * * *